United States Patent [19]

Barriere et al.

[11] Patent Number: 5,786,449

[45] Date of Patent: Jul. 28, 1998

[54] STREPTOGRAMIN DERIVATIVES, THEIR PREPARATION AND PHARMACEUTICAL COMPOSITIONS WHICH CONTAIN THEM

[75] Inventors: Jean-Claude Barriere, Bures-sur-Yvette; Jean-Marc Paris, Vaires-sur-Marne; Gérard Puchault, Marcilly, all of France

[73] Assignee: Rhone-Poulenc Rorer S.A., Antony Cedex, France

[21] Appl. No.: 776,665

[22] PCT Filed: Jul. 31, 1995

[86] PCT No.: PCT/FR95/01025

§ 371 Date: Jan. 31, 1997

§ 102(e) Date: Jan. 31, 1997

[87] PCT Pub. No.: WO96/04299

PCT Pub. Date: Feb. 15, 1996

[30] Foreign Application Priority Data

Aug. 2, 1994 [FR] France .................. 94 09563

[51] Int. Cl.[6] .............. A61K 38/12; C07K 5/00; C07K 7/00; C07K 17/00
[52] U.S. Cl. .................. 530/317; 514/9; 514/11
[58] Field of Search ................ 530/317; 514/9, 514/11

[56] References Cited

U.S. PATENT DOCUMENTS 4,617,290  10/1986  Corbet et al. .............. 514/11

FOREIGN PATENT DOCUMENTS 0133097  7/1984  France .
0248703  12/1987  France .

OTHER PUBLICATIONS

Preud'Homme et al., "Pristinamycine Isolement, Caractérisation et identification des Constituants," Bulletin de la Societe Chimique de France, No. 2, pp. 585–591.

Certified English Translation of above–listed article by Preud'Homme et al., "Pristinamycin: Isolation, Characterization and Identification of the Constituents".

*Primary Examiner*—Robert J. Hill, Jr.
*Assistant Examiner*—S. G. Marshall
*Attorney, Agent, or Firm*—Finnegan, Henderson, Farabow, Garrett & Dunner, L.L.P.

[57] ABSTRACT

Streptogramine derivatives of general formula (I) below, wherein the radical $R_1$ is a methyl or ethyl radical, the radical $R_2$ is a bromine or chlorine atom, or is an alkenyl radical with 3 to 5 carbon atoms when $R_3$ and $R_4$ are methyl, and one of $R_3$ and $R_4$ is a hydrogen atom or a methyl radical and the other is a methyl radical are disclosed. The streptogramine derivatives of general formula (I) have particularly useful antibacterial properties, and may be used in combination with a pristinamycin II derivative.

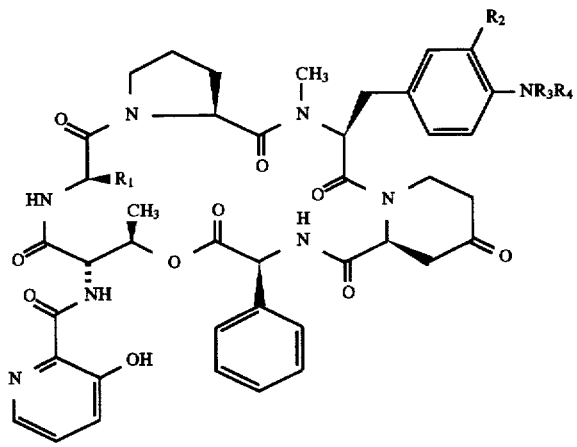

4 Claims, No Drawings

STREPTOGRAMIN DERIVATIVES, THEIR PREPARATION AND PHARMACEUTICAL COMPOSITIONS WHICH CONTAIN THEM

This application is a national stage application filed under 35 U.S.C. § 371 and claims priority of International application number PCT/FR95/01025, filed Jul. 31, 1995.

The present invention relates to streptogramin derivatives of general formula:

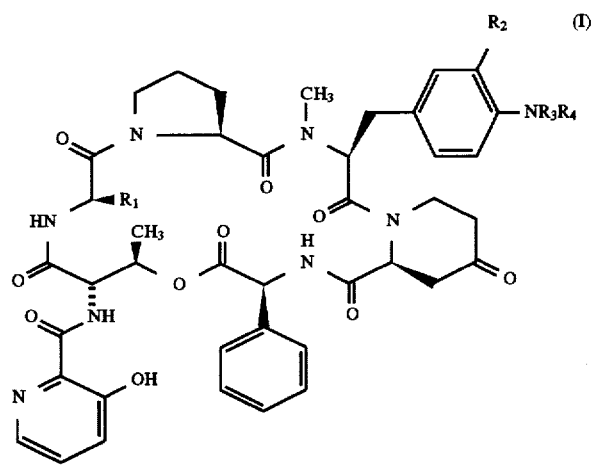

in which the radical $R_1$ denotes a methyl or ethyl radical, the radical $R_2$ denotes a chlorine or bromine atom or denotes an alkenyl radical containing 3 to 5 carbon atoms if $R_3$ and $R_4$ are methyl radicals and the symbols $R_3$ and $R_4$ are: one, a hydrogen atom or a methyl radical and, the other, a methyl radical.

Soluble derivatives belonging to the group B of streptogramins were described previously in European Patent Applications EP 133 097 and EP 248 703. However, by themselves or used in combination with a synergizing component of group A, these derivatives are active only by injectable route and are not, or not very, active orally.

The derivatives of the general formula (I) which are defined above thus open the way to new streptogramins intended for an oral treatment.

According to the invention the streptogramins of general formula (I) in the case of which $R_2$ is a chlorine or bromine atom can be obtained by the action of the corresponding N-halosuccinimide derivative on pristinamycin I in the case of which $R_2$ is a hydrogen atom.

The reaction is performed by means of N-chloro- or N-bromosuccinimide in an organic solvent like, for example, a chlorinated solvent (dichloromethane, dichloroethane, chloroform) or a nitrile (acetonitrile), at a temperature of between 20 and the reflux temperature of the solvent employed.

According to the invention the streptogramins of general formula (I) in the case of which $R_2$ is an alkenyl radical containing 3 to 5 carbon atoms can be obtained by rearrangement in a slightly basic medium of a salt derived from 4-N-alkenylammonio pristinamycin IA of general formula:

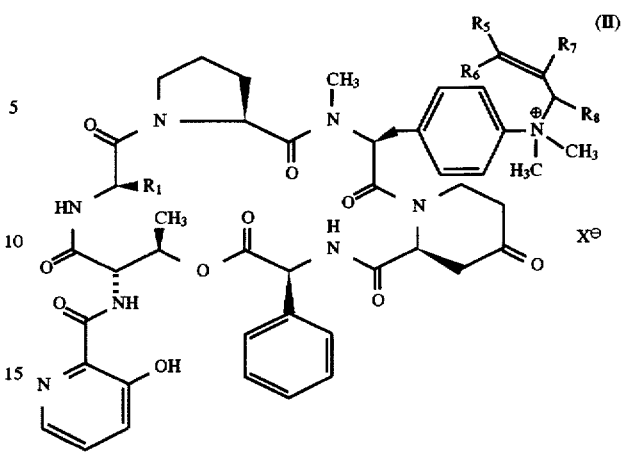

in which $R_1$ is defined as above, $R_5$, $R_6$, $R_7$ and $R_8$ are a hydrogen atom or a methyl radical, provided that at least 2 of them are hydrogen atoms, and $X^\ominus$ denotes an anion, to give the derivative of general formula:

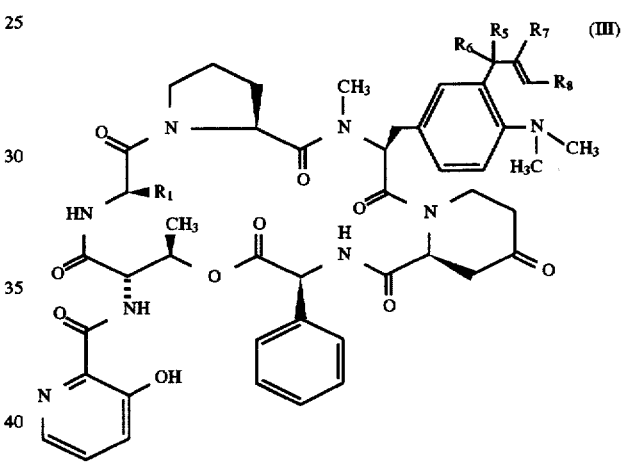

in the case of which $R_1$, $R_5$, $R_6$, $R_7$ and $R_8$ are defined as above.

The reaction is performed by heating at a temperature of between 80° and 100° C. in an aqueous or two-phase medium (for example in ethyl acetate/water medium) in the presence of sodium acetate or of sodium or potassium bicarbonate. A halide of 4-N-alkenylammonio pristinamycin IA is advantageously employed.

The halide of 4-N-alkenylammonio pristinamycin IA can be obtained by the action of an alkenyl halide of general formula:

in the case of which $R_5$, $R_6$, $R_7$ and $R_8$ are defined as above and Hal denotes a halogen atom, on a pristinamycin derivative of general formula:

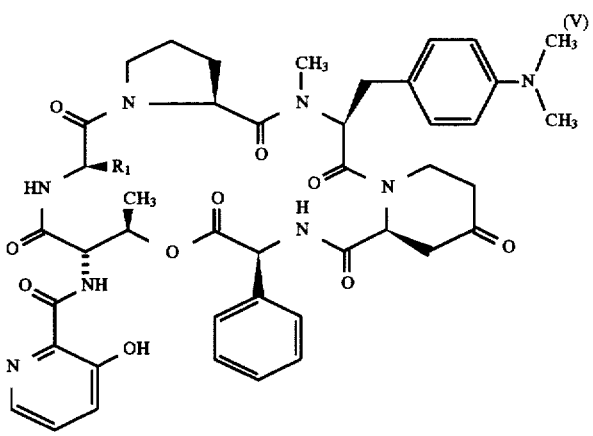

in which R₁ is defined as above.

The reaction is advantageously performed in an organic solvent such as a chlorinated solvent (for example dichloromethane, dichloroethane, chloroform) or an alcohol (for example ethanol) or in a mixture, at a temperature of between 20° C. and the reflux temperature of the reaction mixture. Preferably, a product of general formula (IV) in the case of which Hal is a chlorine or bromine atom is reacted.

The products of general formula (V) are known products, which are described by J. Preud'Homme, P. Tarridec, and A. Belloc, Bull. Soc. Chim. Fr., 2, 585 (1968).

The new streptogramin derivatives of general formula (I) can be purified, if appropriate, by physical methods such as crystallization or chromatography.

The streptogramin derivatives according to the present invention exhibit antibacterial properties and properties of synergizing the antibacterial activity of the derivatives of pristinamycin II.

In vivo, it has been shown that they synergize the antimicrobial activity of pristinamycin II$_B$ on the experimental infections of the mouse with *Staphylococcus aureus* IP 8203 in doses of between 30 and 150 mg/kg orally (30/70 combination).

Their toxicity (LD50) is higher than 1000 mg/kg orally.

The following examples illustrate the preparation of the products according to the invention.

In the examples which follow, the NMR spectra were investigated in deuterochloroform, the nomenclature employed is that of J. O. Anteunis et al., Eur. Biochem., 58, 259 (1975) and especially:

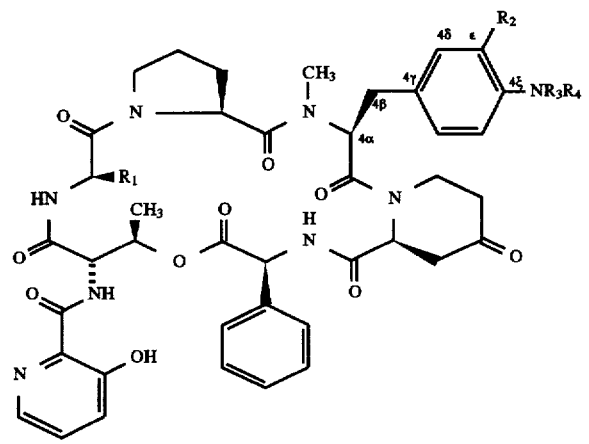

for example, the protons at 4δ and 4ε are respectively named as H₂, H₃ of the aromatic at 4; the flash chromatographies are performed according to W. C. Still et al., J. Org. Chem., 43, 2923 (1978), at a mean nitrogen pressure of 50 kPa using a silica of 40–53 µm particle size; in all cases the flash chromatography follow-up is carried out using thin layer chromatography.

EXAMPLE 1

4ε-chloro pristinamycin I$_A$.

8 g of pristinamycin IA in 80 cm³ of acetonitrile are placed in a round bottom flask and 1.39 g of N-chlorosuccinimide are then added. The mixture is heated to reflux for 16 hours 30 minutes and then 0.12 g of N-chlorosuccinimide are added and the reflux is continued for 3 hours. The reaction mixture is concentrated to dryness at reduced pressure (2.7 kPa) at 30° C. The solid obtained is taken up with 50 cm³ of dichloromethane and 60 cm³ of distilled water to which sodium chloride has been added, the aqueous phase is separated off and then the organic phase is washed with 50 cm³ of distilled water saturated with sodium chloride. The organic phase is separated off, dried over magnesium sulphate, filtered and then concentrated to dryness at reduced pressure (2.7 kPa) at 30° C. to give a yellow solid which is recrystallized from 100 cm³ of 1-propanol at reflux and then a second time from 50 cm³ of 1-propanol at reflux. After cooling, filtration of the crystals and drying at reduced pressure (135 Pa) at 50° C. 3 g of 4ε-chloro pristinamycin I$_A$ are obtained in the form of light-beige crystals melting at 220° C.

Proton N.M.R. spectrum (300 MHz, CDCl₃, δ in ppm): 0.58 (dd, J=16 and 6 Hz, 1H, 5 β₂), 0.91 (t, J=7.5 Hz, 3H: CH₃ 2 γ), from 1.05 to 1.35 (mt, 2H: 3 β₂ and 3 γ₂), 1.32 (d, J=7.5 Hz, 3H: CH₃ 1 γ), from 1.50 to 1.85 (mt, 3H: 3 γ₁ and CH₂ 2 β), 2.03 (mt, 1H, 3 β₁), 2.17 (mt, 1H, 5 δ₂), 2.39 (broad d, J=16 Hz, 1H: 5 δ₁), 2.44 (d, J=16 Hz, 1H: 5 β₁), 2.77 (s, 6H: N(CH₃)₂ 4), 2.85 (dt, J=13.5 and 4.5 Hz, 1H: 5 ε₂), 2.97 (dd, J=12 and 5 Hz, 1H: 4 β₂), 3.23 (s, 3H: NCH₃ 4), 3.35 (t, J=12 Hz, 1H: 4 β₁), 3.30 and 3.58 (2 mts, each 1H: CH₂ 3 δ) , 4.57 (dd, J=8 and 7.5 Hz: 1H, 3 α), 4.76 (broad dd, J=13.5 and 8 Hz, 1H: 5 ε₁), 4.85 (mt, 1H: 2α), 4.90 (dd, J=10 and 1.5 Hz, 1H: 1α), 5.25 (dd, J=12 and 5 Hz, 1H: 4 α), 5.31 (broad d, J=6 Hz, 1H: 5 α), 5.86 (d, J=9.5 Hz, 1H: 6 α), 5.90 (mt, 1H: 1 β), 6.50 (d, J=10 Hz, 1H: NH 2), 6.97 (d, J=8 Hz, 1H: H 5 of the aromatic at 4), 7.08 (dd, J=8 and 2 Hz, 1H: H 6 of the aromatic at 4), from 7.15 to 7.40 (mt, 6H: aromatics H 6 and H 2 of the aromatic at 4), 7.43 (dd, J=8.5 and 2 Hz, 1H: 1' H₄), 7.52 (dd, J=8.5 and 4.5 Hz, 1H: 1' H₅), 7.83 (dd, J=4.5 and 2 Hz, 1H: 1' H₆), 8.38 (d, J=10 Hz, 1H: NH 1), 8.73 (d, J=9.5 Hz, 1H: NH 6), 11.65 (s, 1H: OH).

EXAMPLE 2

4ε-bromo pristinamycin I$_A$ 30 g of pristinamycin I$_A$ in 300 cm³ of dichloromethane are placed in a round bottom flask and then 6.85 g of N-bromosuccinimide are added. The mixture is stirred at ambient temperature for 29 hours and then concentrated to dryness at reduced pressure. The solid obtained is stirred in 400 cm³ of diethyl ether, filtered off and then washed with 2 times 100 cm³ of diethyl ether. After filtration the solid is ground up for 45 minutes in 400 cm³ of distilled water, filtered off and then washed with 2 times 150 cm³ of water. The solid obtained is dried and then recrystallized from 1600 cm³ of ethanol at reflux. After cooling, filtration of the crystals and drying at reduced pressure (135 Pa) at 50° C. 23.2 g of 4ε-bromo pristinamycin I$_A$ are obtained in the form of white crystals melting at 220° C.

Proton N.M.R spectrum (300 MHz, CDCl₃, δ in ppm) : 0.58 (dd, J=16 and 6 Hz, 1H, 5 β₂), 0.91 (t, J=7.5 Hz, 3H:

CH$_3$ 2 γ), from 1.10 to 1.40 (mt, 2H: 3 β$_2$ and 3 γ$_2$) 1.32 (d, J=7.5 Hz, 3H: CH$_3$ 1 γ), from 1.50 to 1.85 (mt, 3H: 3 γ$_1$ and CH$_2$ 2 β), 2.03 (mt, 1H, 3 β$_1$), 2.19 (mt, 1H, 5 δ$_2$), 2.39 (broad d, J=16 Hz, 1H: 5 δ$_1$), 2.44 (d, J=16 Hz, 1H: 5 β$_1$), 2.76 (s, 6H: N(CH$_3$)$_2$ 4), 2.83 (dt, J=13.5 and 4 Hz, 1H: 5 ε$_2$), 2.97 (dd, J=12.5 and 4.5 Hz, 1H: 4 β$_2$), 3.23 (s, 3H: NCH$_3$ 4), 3.30 and 3.57 (2 mts, each 1H: CH$_2$ 3 δ), 3.33 (t, J=12.5 Hz, 1H: 4 β$_1$), 4.55 (dd, J=8 and 7.5 Hz, 1H, 3 α), 4.74 (broad dd, J=13.5 and 8 Hz, 1H: 5 ε$_1$), 4.84 (mt, 1H: 2α), 4.92 (dd, J=10 and 2 Hz, 1H: 1α), 5.27 (dd, J=12.5 and 4.5 Hz, 1H: 4 α), 5.33 (broad d, J=6 Hz, 1H: 5 α), 5.88 (d, J=9.5 Hz, 1H: 6 α), 5.90 (mt, 1H: 1β), 6.53 (d, J=10 Hz, 1H: NH 2), 7.00 (d, J=8 Hz, 1H: H 5 of the aromatic at 4), 7.12 (dd, J=8 and 2 Hz, 1H: H 6 of the aromatic at 4), from 7.15 to 7.40 (mt, 5H: aromatic H 6), 7.43 (dd, J=8.5 and 2 Hz, 1H: 1' H$_4$), 7.46 (d, J=2 Hz, 1H: H 2 of the aromatic at 4), 7.52 (dd, J=8.5 and 4.5 Hz, 1H: 1' H$_5$), 7.87 (dd, J=4.5 and 2 Hz, 1H: 1' H$_6$), 8.41 (d, J=10 Hz, 1H: NH 1), 8.74 (d, J=9.5 Hz, 1H: NH 6), 11.65 (s, 1H: OH).

EXAMPLE 3

4ε-chloro pristinamycin I$_B$

By operating as in Example 1 but starting from 1.7 g of pristinamycin I$_B$, 320 mg of N-chlorosuccinimide in 17 cm$^3$ of acetonitrile and after 1 hour 30 minutes of reflux and then concentration of the reaction mixture to dryness, 1.8 g are obtained of a beige solid which is purified by flash chromatography (98/2 dichloromethane/methanol eluent), to give 1.2 g of 4ε-chloro pristinamycin I$_B$ in the form of a pale yellow solid melting at 198° C.

Proton N.M.R spectrum (400 MHz, CDCl$_3$, δ in ppm): 0.79 (dd, J=16 and 5.5 Hz, 1H, 5 β$_2$), 0.91 (t, J=7.5 Hz, 3H: CH$_3$ 2 γ), 1.15 (mt, 1H: 3 β$_2$), from 1.25 to 1.40 (mt, 1H: 3 γ$_2$), 1.34 (d, J=7.5 Hz, 3H: CH$_3$ 1 γ), from 1.50 to 1.85 (mt, 3H: 3 γ$_1$ and CH$_2$ 2 β), 2.03 (mt, 1H, 3 β$_1$) 2.23 (mt, 1H, 5 δ$_2$), 2.40 (broad d, J=16 Hz, 1H: 5 δ$_1$), 2.47 (d, J=16 Hz, 1H: 5 β$_1$), 2.85 (dt, J=13 and 4 Hz, 1H: 5 ε$_2$) from 2.85 to 2.90 (mt, 1H: 4 β$_2$), 2.88 (s, 3H: ArNCH$_3$ 4), 3.25 (s, 3H: NCH$_3$ 4), 3.28 and 3.58 (2 mts, each 1H: CH$_2$ 3 δ), 3.31 (t, J=12 Hz, 1H: 4 β$_1$), 4.40 (mf, 1H: ArNH), 4.57 (t, J=7.5 Hz, 1H: 3 α), 4.78 (broad dd, J=13 and 8 Hz, 1H: 5 ε$_1$), 4.84 (mt, 1H: 2α), 4.91 (broad d, J=10 Hz, 1H: 1α), 5.23 (dd, J=12 and 5 Hz, 1H: 4 α), 5.36 (broad d, J=5.5 Hz, 1H: 5 α), 5.89 (d, J=9.5 Hz, 1H: 6 α), 5.90 (mt, 1H: 1β), 6.51 (d, J=10 Hz, 1H: NH 2), 6.55 (d, J=8 Hz, 1H: H 5 of the aromatic at 4), 7.0.2 (dd, J=8 and 2 Hz, 1H: H 6 of the aromatic at 4), 7.13 (d, J=2 Hz, 1H: H 2 of the aromatic at 4), from 7.15 to 7.40 (mt, 5H: aromatic H 6), 7.43 (broad d, J=8.5 Hz, 1H: 1' H$_4$), 7.52 (dd, J=8.5 and 4.5 Hz, 1H: 1' H$_5$), 7.79 (broad d, J=4.5 Hz, 1H: 1' H$_6$), 8.40 (d, J=10 Hz, 1H: NH 1), 8.75 (d, J=9.5 Hz, 1H: NH 6), 11.63 (s, 1H: OH).

EXAMPLE 4

4ε-bromo pristinamycin I$_B$

By operating as in Example 2 but starting from 2 g of pristinamycin I$_B$, 420 mg of N-bromosuccinimide in 30 cm$^3$ of dichloromethane and after 1 hour 30 minutes' stirring at ambient temperature and then concentration of the reaction mixture to dryness, 2.1 g are obtained of a beige solid which is purified by flash chromatography (98/2 dichloromethane/methanol eluent) to give 1.7 g of 4ε-bromo pristinamycin I$_B$ in the form of a white solid melting at 220° C.

Proton N.M.R. spectrum (400 MHz, CDCl$_3$, δ in ppm): 0.80 (dd, J=16 and 5.5 Hz, 1H, 5 β$_2$), 0.90 (t, J=7.5 Hz, 3H: CH$_3$ 2 γ), 1.13 (mt, 1H: 3 β$_2$), from 1.20 to 1.40 (mt, 1H: 3γ$_2$), 1.33 (d, J=7.5 Hz, 3H: CH$_3$ 1 γ), from 1.50 to 1.85 (mt, 3H: 3 γ$_1$ and CH$_2$ 2 β), 2.03 (mt, 1H, 3 β$_1$), 2.28 (mt, 1H, 5 δ$_2$), 2.40 (broad d, J=16 Hz, 1H: 5 δ$_1$), 2.46 (d, J=16 Hz, 1H: 5 β$_1$), 2.85 (dt, J=13 and 5 Hz, 1H: 5 ε$_2$), 2.88 (d, J=5.5 Hz, 3H: ArNCH$_3$ 4), 2.90 (dd, J=12 and 4 Hz, 1H: 4 β$_2$), 3.24 (s, 3H: NCH$_3$ 4), 3.30 and 3.58 (2 mts, each 1H: CH$_2$ 3 δ), 3.31 (t, J=12 Hz, 1H: 4 β$_1$) 4.41 (q, J=5.5 Hz, 1H: ArNH), 4.57 (t, J=7.5 Hz, 1H: 3 α), 4.78 (broad dd, J=13 and 8 Hz, 1H: 5 ε$_1$), 4.85 (mt, 1H: 2α), 4.91 (broad d, J=10 Hz, 1H: 1α), 5.24 (dd, J=12 and 4 Hz, 1H: 4 α), 5.37 (broad d, J=5.5 Hz, 1H: 5 α), 5.89 (d, J=9.5 Hz, 1H: 6 α), 5.90 (mt, 1H: 1β), 6.51 (d, J=10 Hz, 1H: NH 2), 6.53 (d, J=8 Hz, 1H: H 5 of the aromatic at 4), 7.0.5 (dd, J=8 and 2 Hz, 1H: H 6 of the aromatic at 4), from 7.15 to 7.40 (mt, 6H: aromatic H 6 and H 2 of the aromatic at 4), 7.43 (broad d, J=8.5 Hz, 1H: 1' H$_4$), 7.48 (dd, J=8.5 and 5 Hz, 1H: 1' H$_5$), 7.79 (broad d, J=5 Hz, 1H: 1' H$_6$), 8.40 (d, J=10 Hz, 1H: NH 1), 8.76 (d, J=9.5 Hz, 1H: NH 6), 11.63 (s, 1H: OH).

EXAMPLE 5

4ε-allyl pristinamycin IA 7.07 g of sodium acetate in 100 cm$^3$ of distilled water are placed in a three-necked flask kept under a nitrogen atmosphere. The solution is brought to reflux and then a solution of 15.5 g of 4-N-allylammonio pristinamycin I$_A$ bromide in 100 cm$^3$ of distilled water is added via a dropping funnel. After 2 hours' reaction 1 g of sodium acetate is added and the mixture is stirred for 22 hours at reflux. A new portion of 5 g of sodium acetate is added and the reaction is continued for 20 hours. The precipitate formed is filtered off hot, rinsed with 2 times 50 cm$^3$ of distilled water and then dried at reduced pressure (2.75 kPa) to give 7 g of a white solid, which is purified by flash chromatography (70/30 toluene/acetone eluent) to give 4.6 g of 4ε-allyl pristinamycin I$_A$ in the form of a white solid melting at 160° C.

Proton N.M.R. spectrum (400 MHz, CDCl$_3$, δ in ppm): 0.42 (dd, J=16 and 5.5 Hz, 1H, 5 β$_2$), 0.92 (t, J=7.5 Hz, 3H: CH$_3$ 2 γ), from 1.15 to 1.40 (mt, 2H: 3 β$_2$ and 3 γ$_2$), 1.33 (d, J=7.5 Hz, 3H: CH$_3$ 1 γ), from 1.55 to 1.80 (mt, 3H: 3 γ$_1$ and CH$_2$ 2 β), from 2.00 to 2.15 (mt, 2H, 3 β$_1$ and 5 δ$_2$), 2.30 (broad d, J=16 Hz, 1H: 5 δ$_1$), 2.33 (d, J=16 Hz, 1H: 5 β$_1$) 2.63 (s, 6H: N(CH$_3$)$_2$ 4), 2.76 (dt, J=13.5 and 4.5 Hz, 1H: 5 ε$_2$), 2.98 (dd, J=12 and 4.5 Hz, 1H: 4 β$_2$), from 3.20 to 3.40 (mt, 3H: 4 β$_1$ - 3 δ$_1$ and 1H of the ArCH$_2$ allyl), 3.25 (s, 3H: NCH$_3$ 4), 3.48 (dd, J=16 and 6.5 Hz, 1H: the other H of the ArCH$_2$ allyl), 3.56 (mt, 1H: 3 δ$_2$), 4.57 (dd, J=6.5 and 7.5 Hz, 1H, 3 α), 4.68 (broad dd, J=13.5 and 7.5 Hz, 1H: 5 ε$_1$), 4.84 (mt, 1H: 2α), 4.90 (broad d, J=10 Hz, 1H: 1α), from 5.00 to 5.15 (mt, 2H: =CH$_2$), 5.23 (broad d, J=5.5 Hz, 1H: 5α), 5.28 (dd, J=12 and 4.5 Hz, 1H 4α), from 5.80 to 5.95 (mt, 3H: 6 α-1β and allyl CH), 6.53 (d, J=10 Hz, 1H: NH 2), 7.04 (mt, 3H: aromatic H at 4), from 7.15 to 7.40 (mt, 5H: aromatic H 6), 7.45 (dd, J=8.5 and 2 Hz, 1H: 1' H$_4$), 7.48 (dd, J=8.5 and 4 Hz, 1H: 1' H—), 7.88 (dd, J=4 and 2 Hz, 1H: 1' H$_6$), 8.45 (d, J=10 Hz, 1H: NH 1), 8.76 (d, J=9.5 Hz, 1H: NH 6), 11.64 (s, 1H: OH).

4-N-Allylammonio pristinamycin I$_A$ bromide can be prepared in the following manner:

10 g of pristinamycin I$_A$ in solution in 25 cm$^3$ of 1,2-dichloroethane are placed in a three-necked flask kept under nitrogen atmosphere, followed by 2.5 cm$^3$ of allyl bromide. The mixture is heated for 7 hours at 40° C. and then stirred at ambient temperature for 14 hours. 200 cm$^3$ of toluene are then added with stirring over 10 minutes and the mixture is stirred for 30 minutes. The precipitate formed is filtered off, rinsed with 50 cm$^3$ of toluene and then dried at reduced pressure (135 Pa) at 45° C. to give 10.5 g of a solid which is ground up in 200 cm$^3$ of ethyl acetate at 40° C. and then at ambient temperature for 1 hour. The solid is filtered off and then dried at 45° C. at reduced pressure (135 Pa) to give 10 g of 4-N-allylammonio pristinamycin IA bromide in the form of a white solid melting at about 210° C.

Proton N.M.R. spectrum (400 MHz, CDCl$_3$ with addition of a few drops of CD$_3$ OD d4, δ in ppm): 0.75 (t, J=7.5 Hz, 3H: CH$_3$ 2 γ), from 1.00 to 1.35 (mt, 3H: 3 β$_2$ - 3 γ$_2$ and 5 β$_2$), 1.18 (d, J=7.5 Hz, 3H: CH$_3$ 1 γ), from 1.45 to 1.65 (mt, 3H: 3 γ$_1$ and CH$_2$ 2 β), 1.95 (mt, 1H: 3 β$_1$) 2.15 (mt, 1H: 5 δ$_2$), 2.28 (broad d, J=16 Hz, 1H: 5 δ$_1$) 2.55 (d, J=16 Hz, 1H: 5 β$_1$), 2.72 (dt, J=13.5 and 4.5 Hz, 1H: 5 ε$_2$), 2.95 (s, 3H: NCH$_3$ 4), from 3.10 to 3.50 (mt, 4H: CH$_2$ 4 β and CH$_2$ 3 δ), 3.40 and 3.48 (2s, 6H in all: N(CH$_3$)$_2$ 4), 4.35 (t, J=7.5 Hz, 1H: 3 α), from 4.40 to 4.60 (mt, 3H: NCH$_2$ allyl and 5 ε$_1$), 4.64 (mt, 1H: 2 α), 4.93 (broad s, 1H: 1α), from 5.30 to 5.75 (mt, 7H: CH$_2$ allyl - 5 α - 4 α - 6 α - 1β and allyl CH), 6.88 (d, J=10 Hz, 1H: NH 2), from 7.05 to 7.25 (mt, 8H: aromatic H 6 - 1' H$_4$ and 4 δ), 7.35 (dd, J=8 and 4 Hz, 1H: 1' H$_5$), 7.60 (d, J=8.5 Hz, 2H: 4 ε), 7.65 (mt, H: 1' H$_6$), 8.58 (d, J=9.5 Hz, 1H: NH 6).

EXAMPLE 6

4ε-(2-methylprop-2-en-1-yl) pristinamycin I$_A$

By operating as in Example 5 but starting from 4.31 g of 4N-(2-methylprop-2-en-1-yl)ammonio pristinamycin I$_A$ chloride and 1.64 g of sodium acetate in 40 cm$^3$ of distilled water, 2.45 g are obtained of a solid which is purified by flash chromatography (50/50 toluene/acetone eluent) to give 515 mg of 4ε-(2-methylprop-2-en-1-yl) pristinamycin I$_A$ in the form of a white solid melting at a temperature higher than 260° C.

Proton N.M.R. spectrum (400 MHz, CDCl$_3$, δ in ppm): 0.45 (dd, J=16 and 5.5 Hz, 1H, 5 β$_2$), 0.90 (t, J=7.5 Hz, 3H: CH$_3$ 2 γ), from 1.15 to 1.40 (mt, 2H: 3 β$_2$ and 3 γ$_2$), 1.33 (d, J=7.5 Hz, 3H: CH$_3$ 1 γ), from 1.55 to 1.80 (mt, 3H: 3 γ$_1$ and CH$_2$ 2 β), 1.66 (s, 3H: CH$_3$), from 2.00 to 2.15 (mt, 2H, 3 β$_1$ and 5 δ$_2$), 2.31 (very broad d, J=16 Hz, 2H: 5 δ$_1$ and 5 β$_1$), 2.62 (s, 6H: N(CH$_3$)$_2$ 4), 2.78 (dt, J=13 and 4 Hz, 1H: 5 ε$_2$), 2.99 (dd, J=12 and 3.5 Hz, 1H: 4 β$_2$), 3.23 and 3.44 (2d, J=15.5 Hz, 1H each: ArCH$_2$), 3.27 (s, 3H: NCH$_3$ 4), 3.32 and 3.56 (2 mts, 1H each: CH$_2$ 3 δ), 3.33 (t, J=12 Hz, 1H: 4 β$_1$), 4.58 (t, J=7.5 Hz, 1H, 3 α), 4.60 and 4.82 (2 broad s, 1H each: =CH$_2$), 4.70 (broad dd, J=13 and 7.5 Hz, 1H: 5 ε$_1$), 4.84 (mt, 1H: 2α), 4.90 (broad d, J=10 Hz, 1H: 1α), 5.23 (broad d, J=5.5 Hz, 1H: 5α), 5.25 (dd, J=12 and 3.5 Hz, 1H: 4α), 5.87 (d, J=9.5 Hz, 1H: 6 α), 5.89 (mt, 1H: 1β), 6.52 (d, J=10 Hz, 1H: NH 2), 7.02 (mt, 3H: aromatic H 4), from 7.15 to 7.40 (mt, 5H: aromatic H 6), 7.45 (broad d, J=8.5 Hz, 1H: 1' H$_4$), 7.49 (dd, J=8.5 and 4.5 Hz, 1H: 1' H$_5$), 7.88 (mt, 1H: 1' H$_6$), 8.45 (d, J=10 Hz, 1H: NH 1), 8.76 (d, J=9.5 Hz, 1H: NH 6), 11.64 (s, 1H: OH).

4N-(2-Methylprop-2-en-1-yl)ammonio pristinamycin I$_A$ chloride can be prepared in the following manner:

In a three-necked flask kept under nitrogen atmosphere are placed 8.66 g of pristinamycin I$_A$ in solution in 40 cm$^3$ of dichloromethane and 20 cm$^3$ of methanol and then 9.8 cm$^3$ of β-methyllal chloride. The mixture is stirred at reflux for 48 hours and then concentrated at reduced pressure (2.7 kPa) at 30° C. The solid obtained is dissolved in 30 cm$^3$ of dichloromethane and 300 cm$^3$ of toluene are then added dropwise with stirring. After an hour's stirring the solid obtained is filtered off, rinsed 3 times with 30 cm$^3$ of toluene and then with 50 cm$^3$ of diethyl ether. The solid is filtered off and then dried at 45° C. at reduced pressure (135 Pa) to give 4.34 g of crude 4N-(2-methylprop-2-en-1-yl)ammonio pristinamycin I$_A$ chloride in the form of a yellow solid, employed in this form for the preparation of 4ε-(2-methylprop-2-en-1-yl) pristinamycin I$_A$.

EXAMPLE 7

4ε-[(2-RS)-but-3-en-2-yl) pristinamycin I$_A$:

By operating as in Example 5 but starting from 4.8 g of 4-N-(buten-2-yl)ammonio pristinamycin I$_A$ bromide and 3.69 g of sodium acetate in 100 cm$^3$ of distilled water, 2.37 g are obtained of a solid which is purified by flash chromatography (55/45 toluene/acetone eluent) to give 254 mg of 4ε-[(2-RS)-but-3-en-2-yl) pristinamycin I$_A$ in the form of a white solid melting at a temperature higher than 260° C.

Proton N.M.R. spectrum (400 MHz, CDCl$_3$, δ in ppm): the 50/50 mixture of the two diastereoisomers is seen. 0.42 and 0.48 (2 dd, J=16 and 5.5 Hz, 1H in all, 5 β$_2$) 0.90 (t, J=7.5 Hz, 3H: CH$_3$ 2 γ), 1.22 (d, J=7.5 Hz, 3H: CH$_3$), from 1.15 to 1.40 (mt, 2H: 3 β$_2$ and 3 γ$_2$), 1.37 (d, J=7.5 Hz, 3H: CH$_3$ 1 γ), from 1.55 to 1.80 (mt, 3H: 3 γ$_1$ and CH$_2$ 2 β), from 2.00 to 2.15 (mt, 2H, 3 β$_1$ and 5 δ$_2$), from 2.15 to 2.40 (mt, 2H: 5 δ$_1$ and 5 β$_1$), 2.62 (s, 6H: N(CH$_3$)$_2$ 4), 2.72 and 3.00 (2 mts, 1H in all: 5 ε$_2$), 3.05 and from 3.20 to 3.40 (2 mts, 3H in all: 4 β$_2$ - 4 β$_1$ and 3 δ$_2$), 3.27 (s, 3H: NCH$_3$ 4), 3.57 (mt, 1H: 3 δ$_1$), 4.10 (mt, 1H: ArCH), 4.60 (t, J=7.5 H, 1H, 3 α), 4.64 (broad dd, J=13 and 8 Hz, 1H: 5 ε$_1$), from 4.75 to 5.55 (mt, 6H: =CH$_2$ - 2α - 1α - 5 α and 4α), from 5.85 to 6.05 (mt, 3H: 6 α - 1β and CH=), from 6.45 to 6.60 (mt, 1H: NH 2), 7.05 (mt, 3H: aromatic H 4), from 7.15 to 7.40 (mt, 5H: aromatic H 6), 7.45 (mt, 2H: 1' H$_4$ and 1' H$_5$), 7.98 and 8.02 (2 mts, 1H in all: 1' H$_6$), 8.53 and 8.57 (2d, J=10 Hz, 1H in all: NH 1), 8.82 and 8.85 (2d, J=9.5 Hz, 1H in all: NH 6), 11.62 and 11.66 (2s, 1H in all: OH).

4-N-(Buten-2-yl)ammonio pristinamycin I$_A$ bromide can be prepared in the following manner:

By operating as in Example 6 but starting from 8.66 g of pristinamycin I$_A$, 40 cm$^3$ of dichloromethane, 20 cm$^3$ of methanol and 10.3 cm$^3$ of crotyl bromide and after 8 hours' stirring at ambient temperature and then evaporation, a solid is obtained, which is dissolved in 40 cm$^3$ of dichloromethane. 400 cm$^3$ of toluene are added dropwise with stirring to this solution. After an hour's stirring the precipitate obtained is filtered off, rinsed 3 times with 30 cm$^3$ of toluene and then with 50 cm$^3$ of diethyl ether. The solid is filtered off to give 10.7 g of crude 4-N-(buten-2-yl)ammonio pristinamycin I$_A$ bromide in the form of a light-beige solid employed in this form in the preparation of 4ε-[(2-RS)-but-3-en-2-yl) pristinamycin I$_A$.

The present invention also relates to the medications consisting of the derivatives of streptogramins according to the invention, in the pure state, used in combination with a derivative of pristinamycin II and/or in the form of a combination with any compatible and pharmaceutically acceptable diluent or adjuvant. The medications according to the invention can be employed orally, rectally or topically.

Tablets, pills, powders or granulates may be employed as compositions for oral administration. In these compositions the active product, optionally in the form of a combination, is mixed with one or a number of inert diluents or adjuvants such as sucrose, lactose or starch. These compositions may also include substances other than diluents, for example a lubricant such as magnesium stearate.

Compositions for rectal administration are suppositories or rectal capsules which, besides the active product contain excipients such as cocoa butter, semisynthetic glycerides or polyethylene glycols.

Compositions for topical administration may be, for example, creams, ointments, lotions or aerosols.

In human therapeutics the new streptogramin derivatives according to the invention are particularly useful in the treatment of infections of bacterial origin. The doses depend on the effect sought after and the duration of the treatment. The doses are generally between 0.4 and 3.5 g of active product in 2 or 3 portions per day, orally for an adult.

In general, the medical practitioner will determine the posology which he or she considers most appropriate as a function of the age, weight and of all the other factors specific to the individual to be treated.

The following example illustrates a composition according to the invention.

EXAMPLE

Tablets containing a 250 mg dose of active product, which have the following composition, are prepared according to the usual technique:

| | |
|---|---|
| 4ε-allyl pristinamycin $I_A$ | 250 mg |
| pristinamycin $II_B$ | 75 mg |
| excipient: starch, hydrated silica, dextrin, gelatin, magnesium stearate: q.s. | 500 mg |

We claim:
1. A streptogramin derivative of formula (I):

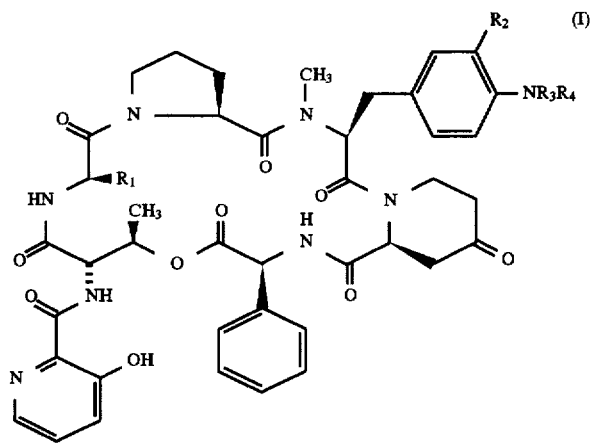

in which $R_1$ denotes a methyl or ethyl radical;

$R_2$ denotes a chlorine or bromine atom, or, when $R_3$ and $R_4$ are both methyl radicals, $R_2$ denotes an alkenyl radical containing 3 to 5 carbon atoms; and $R_3$ and $R_4$ are selected such that one of $R_3$ and $R_4$ denotes a hydrogen atom or a methyl radical and the other denotes a methyl radical.

2. A process for preparing a streptogramin derivative of formula (I) according to claim 1, wherein $R_2$ is a chlorine or bromine atom, said process comprising the step of reacting the N-halosuccinimide of said streptogramin derivative with pristinamycin I, wherein $R_2$ is a hydrogen atom.

3. A process for preparing a streptogramin derivative of formula (I) according to claim 1, wherein $R_2$ is an alkenyl radical containing 3 to 5 carbon atoms, said process comprising the step of rearranging, in a basic medium, a salt derived from 4-N-alkenylammonio pristinamycin IA of formula (11):

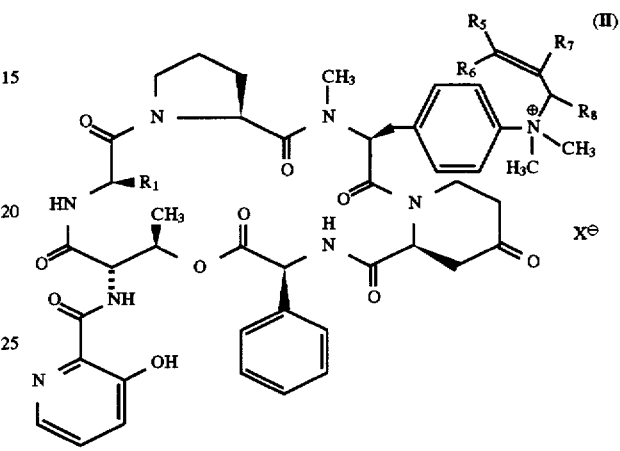

in which $R_1$ is defined as in claim 1; $R_5$, $R_6$, $R_7$ and $R_8$ are each independently a hydrogen atom or a methyl radical, provided that at least two of $R_5$, $R_6$, $R_7$, and $R_8$ are hydrogen atoms; and $X^\ominus$ denotes an anion.

4. A pharmaceutical composition comprising a pharmaceutically effective amount of at least one streptogramin derivative according to claim 1, wherein the streptogramin derivative is in the pure state or is in combination with a derivative of pristinamycin II, together with at least one compatible and pharmaceutically acceptable diluent or adjuvant.

* * * * *